(12) United States Patent
Kovacich et al.

(10) Patent No.: US 9,870,885 B2
(45) Date of Patent: Jan. 16, 2018

(54) VACUUM LOSS DETECTION

(71) Applicant: Cooper Technologies Company, Houston, TX (US)

(72) Inventors: John Albert Kovacich, Waukesha, WI (US); Paul Newcomb Stoving, Oak Creek, WI (US); Christopher Randall Hastreiter, South Milwaukee, WI (US); Rose Ellen Weisburgh, Washington, DC (US); Robert Raymond Schuetz, West Allis, WI (US); Lisa Carol Sletson, Waterford, WI (US); Ross Stuart Daharsh, South Milwaukee, WI (US)

(73) Assignee: Cooper Technologies Company, Houston, TX (US)

( * ) Notice: Subject to any disclaimer, the term of this patent is extended or adjusted under 35 U.S.C. 154(b) by 283 days.

(21) Appl. No.: 14/708,770

(22) Filed: May 11, 2015

(65) Prior Publication Data

US 2015/0325394 A1    Nov. 12, 2015

Related U.S. Application Data

(60) Provisional application No. 61/991,884, filed on May 12, 2014.

(51) Int. Cl.
*H01H 33/668* (2006.01)
*G01N 27/02* (2006.01)
*H01H 33/662* (2006.01)

(52) U.S. Cl.
CPC ......... *H01H 33/668* (2013.01); *G01N 27/021* (2013.01); *H01H 33/66207* (2013.01)

(58) Field of Classification Search
CPC ........... H01H 33/668; H01H 33/66207; G01N 27/021

(Continued)

(56) References Cited

U.S. PATENT DOCUMENTS 3,641,350 A    2/1972   Petropoulas
3,747,410 A *  7/1973   Nissen .................... G01L 21/00
                                                    338/36

(Continued)

FOREIGN PATENT DOCUMENTS

JP      2000-121606 A     4/2000
KR      2010-0096610 A    9/2010

OTHER PUBLICATIONS

International Search Report & Written Opinion, counterpart International Patent Application No. PCT/US2015/030121, dated Aug. 26, 2015, 13 pages.

*Primary Examiner* — Lisa Caputo
*Assistant Examiner* — Nathaniel T Woodward
(74) *Attorney, Agent, or Firm* — DiBerardino McGovern IP Group LLC

(57) ABSTRACT

Techniques for detecting vacuum loss in a vacuum interrupter are disclosed. For example, a sensing system of a vacuum interrupter includes a sensor including a material that oxidizes in the presence of air and is at least partially positioned in an evacuated space of a vacuum interrupter, the sensor being configured to produce an indication of impedance of the material; and a control system coupled to the sensor, the control system including an electronic processor and an electronic storage that stores instructions that, when executed, cause the electronic processor to access an indication of impedance produced by the sensor, determine a measure of impedance of the material of the sensor based on the accessed indication of impedance, and determine a condition of the evacuated space based on the determined measure of impedance.

25 Claims, 12 Drawing Sheets

(58) Field of Classification Search
USPC .................................................. 73/40.5 R
See application file for complete search history.

(56) References Cited

U.S. PATENT DOCUMENTS

| | | | |
|---|---|---|---|
| 3,822,146 A * | 7/1974 | Nissen et al. | H05H 7/04 |
| | | | 427/292 |
| 3,983,345 A | 9/1976 | Phillips | |
| 4,096,366 A | 6/1978 | Titus | |
| 4,103,291 A | 7/1978 | Howe | |
| 4,163,130 A | 7/1979 | Kubota | |
| 4,402,224 A | 9/1983 | Fukushima | |
| 4,403,124 A | 9/1983 | Perkins | |
| 4,440,995 A * | 4/1984 | Lange | H01H 33/668 |
| | | | 218/122 |
| 4,471,309 A | 9/1984 | Lange | |
| 4,484,818 A | 11/1984 | Houston | |
| 4,491,704 A | 1/1985 | Milianowicz | |
| 4,547,769 A | 10/1985 | Tanigaki | |
| 4,553,139 A | 11/1985 | Tanigaki | |
| 4,937,698 A | 6/1990 | Toya | |
| 5,286,933 A | 2/1994 | Pham | |
| 5,344,549 A * | 9/1994 | Dees | G01N 27/4075 |
| | | | 204/424 |
| 6,418,791 B1 | 7/2002 | Lanni | |
| 6,952,101 B2 | 10/2005 | Gupta | |
| 6,952,102 B2 | 10/2005 | Sakaki | |
| 7,148,677 B2 | 12/2006 | Marchand | |
| 7,225,676 B2 | 6/2007 | Randazzo | |
| 7,253,630 B1 | 8/2007 | Zhou | |
| 7,313,964 B2 | 1/2008 | Montesclaros | |
| 7,322,248 B1 * | 1/2008 | Long | G01L 21/12 |
| | | | 324/610 |
| 7,332,906 B2 | 2/2008 | Marchand | |
| 7,383,733 B2 | 6/2008 | Mosely | |
| 7,473,863 B2 | 1/2009 | Schreiber | |
| 7,497,122 B2 | 3/2009 | Montesclaros | |
| 7,499,255 B2 | 3/2009 | Domo | |
| 7,802,480 B2 * | 9/2010 | Mosely | H01H 33/668 |
| | | | 218/121 |
| 8,450,630 B2 | 5/2013 | Stoving | |
| 8,658,932 B2 | 2/2014 | Schellekens | |
| 2003/0173969 A1 * | 9/2003 | Sakaki | H01H 33/668 |
| | | | 324/409 |
| 2007/0202012 A1 | 8/2007 | Steichen | |
| 2011/0088416 A1 * | 4/2011 | Koethler | F24F 11/0086 |
| | | | 62/80 |
| 2011/0259086 A1 | 10/2011 | Harris | |
| 2012/0145674 A1 | 6/2012 | Schellekens | |
| 2013/0147590 A1 | 6/2013 | Ledbetter | |
| 2013/0341206 A1 * | 12/2013 | Schenk | G01N 27/30 |
| | | | 205/780.5 |

* cited by examiner

VACUUM LOSS DETECTION

CROSS-REFERENCE TO RELATED APPLICATION

This application claims the benefit of U.S. Provisional Application No. 61/991,884, filed on May 12, 2014 and titled VACUUM LOSS DETECTION, which is incorporated herein by reference in its entirety.

TECHNICAL FIELD

This disclosure relates to vacuum loss detection in a vacuum interrupter.

BACKGROUND

A vacuum interrupter may be used to protect electrical systems from electrical fault conditions, which may produce damaging high current or voltage transients. The vacuum interrupter includes a stationary contact and a movable contact, both of which are enclosed in a vessel designed to hold a vacuum. The movable contact moves relative to the stationary contact, moving the contacts into and out of electrical contact with each other. In this manner, the vacuum interrupter may interrupt the high current flow to the electrical system by opening the contacts.

SUMMARY

In one general aspect, a sensing system of a vacuum interrupter includes a sensor including a material that oxidizes in the presence of air and is at least partially positioned in an evacuated space of a vacuum interrupter, the sensor being configured to produce an indication of impedance of the material; and a control system coupled to the sensor, the control system including an electronic processor and an electronic storage that stores instructions that, when executed, cause the electronic processor to access an indication of impedance produced by the sensor, determine a measure of impedance of the material of the sensor based on the accessed indication of impedance, and determine a condition of the evacuated space based on the determined measure of impedance.

To determine a condition of the evacuated space, the processor may determine whether a pressure of the evacuated space has increased based on the determined measure of impedance.

The indication of impedance and the determination of a measure of impedance of the material based on the accessed indication of impedance relate directly to the detection of vacuum loss in a vacuum interrupter.

Implementations may include one or more of the following features. The indication of impedance may include one of a voltage across the sensor or a current through the material, and the determined measure of impedance may include an impedance of the material.

The sensor may include a plurality of contacts that are held in physical contact with each other, each of the plurality of contacts including the material that oxidizes in the presence of air.

The sensor may include a contact and one or more of an endcap and a shield of the vacuum interrupter.

In some implementations, the electronic storage also stores a second measure of impedance, a threshold difference, and instructions that, when executed, cause the electronic processor to compare the determined measure of impedance to the second measure of impedance to determine a difference in impedance, and if the determined difference is equal to or greater than the threshold difference, generate a signal that is sufficient to provide information to take a switchgear that includes the vacuum interrupter out of service. The second measure of impedance may be a measure of impedance determined based on an accessed measure of impedance obtained from the sensor at an earlier time.

The electronic storage may further store a threshold measure of impedance and instructions that, when executed, cause the electronic processor to compare the determined measure of impedance to the threshold measure of impedance, and if the determined measure of impedance is equal to or greater than the threshold impedance, generate a signal that is sufficient to provide information to take a switchgear that includes the vacuum interrupter out of service.

In another general aspect, a method of detecting a loss of vacuum in a vacuum interrupter includes measuring an indication of impedance of a material that oxidizes in the presence of air and is enclosed in an evacuated space that is internal to a vacuum interrupter; determining, based on the measured indication of impedance of the material, an indication of pressure of the evacuated space; and generating a signal based on the determined indication of pressure.

Implementations may include one or more of the following features. The measured indication of impedance may include a temperature of the material. The measured indication of impedance may be one or more of a voltage, a current, a conductivity, and a resistivity.

The method also may include measuring a second indication of impedance of the material that oxidizes in air; comparing the measured indication of impedance to the second measured indication of impedance to determine a difference between the second measured indication of impedance and the measured indication of impedance; comparing the magnitude of the difference to a threshold value; and, when the magnitude of the difference equals or exceeds the threshold, generating a signal that is sufficient to provide information to take a switchgear that includes the vacuum interrupter out of service.

The vacuum interrupter may include main contacts that open to prevent current from flowing through the vacuum interrupter and close to permit current to flow through the vacuum interrupter, and the material that oxidizes in air may be separate and distinct from the main contacts.

The vacuum interrupter may include main contacts that open to prevent current from flowing through the vacuum interrupter and close to permit current to flow through the vacuum interrupter, the indication of impedance may include temperature, and the material that oxidizes in air may include a portion of the main contacts.

In another general aspect, a vacuum interrupter includes a stationary contact; a movable contact configured to move relative to the stationary contact between an open position and a closed position, the stationary contact and the movable contact being separated in the open position and being in contact in the closed position; a vessel that encloses the movable contact and the stationary contact in an evacuated space; and a sensor configured to produce an indication of impedance of a region in the evacuated space.

Implementations may include one or more of the following features. The sensor may include a material that oxidizes in the presence of air and is configured to produce an indication of impedance of the material. The sensor may be configured to produce the indication of impedance in one or more of the open position and the closed position. The sensor may be configured to communicate with a controller.

The indication of impedance may be one or more of an amount of current passing through the sensor, a voltage across the sensor, a conductivity of the sensor, an impedance of the sensor, a temperature of the sensor, and a temperature of a region in the vicinity of the sensor or vacuum interrupter.

In some implementations, the sensor includes contacts that are physically separated from each other by a gap, the contacts of the sensor being separate and distinct from the movable contact and the stationary contact, and the indication of impedance of a region in the evacuated space includes a voltage across the contacts of the sensor. The vessel of the vacuum interrupter may include one or more endcaps and a shield, and one of the contacts of the sensor may be one of the endcaps or the shield. The indication of impedance may include a breakdown voltage of the evacuated space.

In another general aspect, a system includes a vacuum interrupter and a control system. The vacuum interrupter includes a stationary contact; a movable contact configured to move relative to the stationary contact between an open position and a closed position, the stationary contact and the movable contact being separated in the open position and being in contact in the closed position; a vessel that encloses the movable contact and the stationary contact in an evacuated space; and a sensor configured to produce an indication of impedance of a region that is in the evacuated space. The control system is coupled to the sensor and configured to receive data from and to provide data to the sensor, the control system including an electronic processor and an electronic storage that stores instructions that, when executed, cause the electronic processor to access the indication of impedance of the region that is in the evacuated space, and determine a condition of the evacuated space based on the accessed indication of impedance.

Implementations may include one or more of the following features. The sensor may be in the evacuated space. The sensor may include a thermal sensor. The system also may include an insulator that at least partially surrounds the vessel, and the sensor that is configured to measure a temperature may be positioned in the insulator and outside of the evacuated space. Implementations of any of the techniques described above may include a switchgear device, a vacuum interrupter, a vacuum sensing system, a sensor of a vacuum interrupter, a controller configured to be coupled to a vacuum interrupter, instructions stored on a non-transitory computer-readable medium, and/or a method. The details of one or more implementations are set forth in the accompanying drawings and the description below. Other features will be apparent from the description and drawings, and from the claims.

DRAWING DESCRIPTION

Like reference numbers indicate like elements.

DETAILED DESCRIPTION

Figure 1:
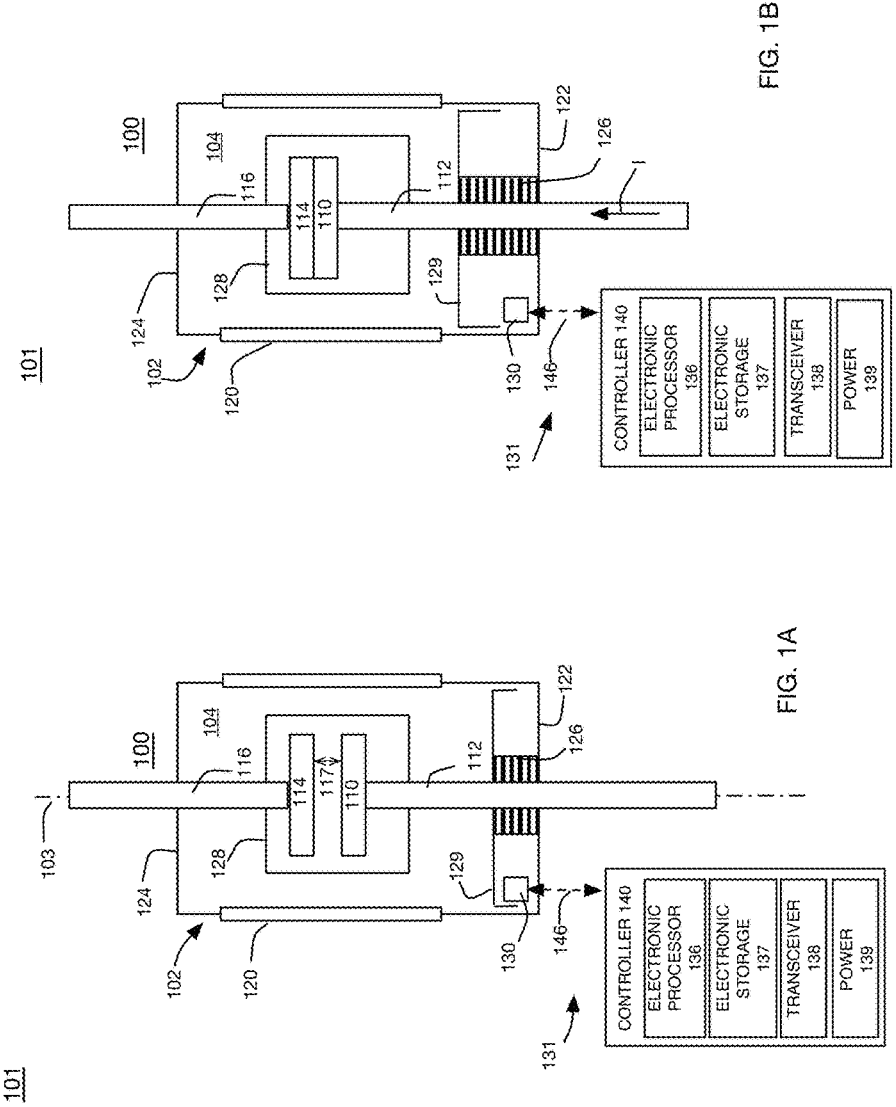
FIG. 1A is a block diagram of an exemplary system that includes a vacuum sensing system and a vacuum interrupter in an open position.
FIG. 1B is a block diagram of the system of FIG. 1A with the vacuum interrupter in a closed position.

FIGS. 1A and 1B are block diagrams of a system 101 that includes a vacuum interrupter 100 and a vacuum sensing system 131. The vacuum interrupter 100 includes a vessel 102 that is designed to maintain a vacuum seal with respect to components enclosed therein. Air is removed from the vessel 102, leaving an evacuated space 104. For the vacuum interrupter 100 to work optimally, the pressure of the evacuated space 104 should be as low as possible, to maintain a vacuum or near vacuum condition in the vessel 102. As discussed in more detail below, the vacuum sensing system 131 monitors a condition of the evacuated space 104 to detect a loss of this vacuum or near vacuum state. In other words, the vacuum sensing system 131 monitors the evacuated space 104 for an increase in the pressure in an indirect manner. For example, the vacuum sensing system 131 may measure current, voltage, resistivity, impedance, continuity, and/or temperature to obtain an indirect indication of a change in the pressure in the vessel 102.

The vessel 102 encloses a movable contact 110 and a stationary contact 114, which are respectively connected to a movable rod 112 and a stationary rod 116. The movable rod 112 is operable to move the movable contact 110 relative to the stationary contact 114 and the stationary rod 116, thereby permitting or preventing current flow through the vacuum interrupter 100. When the vacuum interrupter 100 is in an open position (FIG. 1A), the contacts 110, 114 are separated by a gap 117. When the vacuum interrupter 100 is in a closed position (FIG. 1B), the contacts 110, 114 make physical contact and current flows (I) through the vacuum interrupter 100.

The vessel 102 also includes an electrical insulator 120 and endcaps 122, 124 that seal the insulator 120. The insulator 120 may be, for example, a ceramic, or a dielectric material, and the endcaps 122, 124 may be brazed to a metalized surface of the insulator 120. A flexible bellows 126 extends from the endcap 122 into the vessel 102 and allows the movable rod 112 to move through the endcap 122 without the vessel 102 losing the vacuum seal.

The vessel 102 also includes a central shield 128, which helps to contain arcs that can form between the contacts 110, 114 when the vacuum interrupter 100 is in the open position. A shield 129 protects the bellows 126 and the sensor 130 from the arcs. In the example shown, the shield 129 extends radially from a longitudinal axis 103 of the vacuum interrupter 100 and is positioned between the sensor 130 and the contacts 110, 114.

During operation of the vacuum interrupter 100, the pressure of the evacuated space 104 should be maintained at a pressure that is sufficiently low that the evacuated space 104 provides electrical insulation to help prevent and extinguish arcs between the contacts 110, 114 when they are in the open position. For example, the pressure of the evacuated space 104 may be at a pressure that has a high voltage withstand (or high breakdown voltage). The breakdown voltage is the voltage necessary to start a discharge or arc between the electrodes. To provide such insulation, the pressure of the evacuated space 104 may be, for example, on the order of $10^{-8}$ atmosphere, or $10^{-5}$ Torr. If the pressure of the evacuated space 104 rises, the breakdown voltage can decrease, making arcing between the contacts 110, 114 more difficult to extinguish and degrading performance of the vacuum interrupter 100. For example, in implementations in which the gap 117 is 10 millimeters (mm), when the pressure of the evacuated space 104 reaches around $2.7\times10^{-4}$ atmospheres (about 0.20 Torr), the breakdown voltage of the evacuated space 104 may have decreased to the point where performance of the vacuum interrupter 100 begins to degrade. Thus, if the pressure of the evacuated space 104 rises, for example, due to a leak in the vessel 102 that allows air and/or other fluids to flow into the vessel 102, the vacuum interrupter 100 may malfunction or become inoperable.

The vacuum sensing system 131 monitors the condition of the evacuated space 104 so that the vacuum interrupter 100 is monitored for its operation suitability in the field. The vacuum sensing system 131 may be used to monitor the condition of the evacuated space 104 while the vacuum interrupter 100 is in operation, regardless of whether the interrupter 100 is in an open position (FIG. 1A) or closed position (FIG. 1B). Additionally, the vacuum sensing system 131 allows the condition of the evacuated space 104 of the vessel 102 to be monitored remotely and on a continuous, discrete, or on-demand basis.

The vacuum sensing system 131 includes a sensor 130 that measures an indication of impedance of a region inside of the vessel 102. The indication of impedance or a change in the value of the indication of impedance may be used to detect a partial or complete loss of the vacuum in the vessel 102, or a rise in the pressure of the evacuated space 104. The region inside the vessel 102 may be the sensor 130 itself and/or a region in the vicinity of the sensor 130. The sensor 130 may measure, for example, a current passing through the sensor 130, a voltage across the sensor 130, a resistance and/or continuity of the sensor 130, an impedance of the sensor 130, a high-frequency impedance of the sensor 130, and/or a temperature of a component in the vicinity of the vacuum interrupter 100.

For example, the sensor 130 may include a sensing element with a material that oxidizes in the presence of air that enters the vessel 102 during a leak. The oxidation causes the resistance of the material included in the sensor 130 to increase, thus changing the value of the indication of impedance (for example, current, and voltage) produced by the sensor 130. In this manner, the indication of impedance changes as a result of the leak, allowing the sensor 130 to monitor the condition of the evacuated space 104.

The indication of impedance provided by the sensor 130 can be used to detect small pressure changes in the vessel 102 that lead up to loss of the evacuated space 104. The interrupting and insulation properties of the evacuated space 104 are determined by Paschen's Law, which is expressed in Equation (1):

$$V=(a*pd)/[\ln(pd)+b], \quad (1)$$

where V is the breakdown voltage in volts, a and b are constants for particular gasses, and pd is the product of pressure (in Atmospheres) times the length of the electrode gap in meters. The breakdown voltage is the voltage necessary to start a discharge or arc between the electrodes. In the context of a vacuum interrupter, the electrode gap may be the spacing between the movable contact and the stationary contact (such as the gap 117 between the contacts 110, 114 of FIG. 1A) or between any other two potentials.

Figure 2:
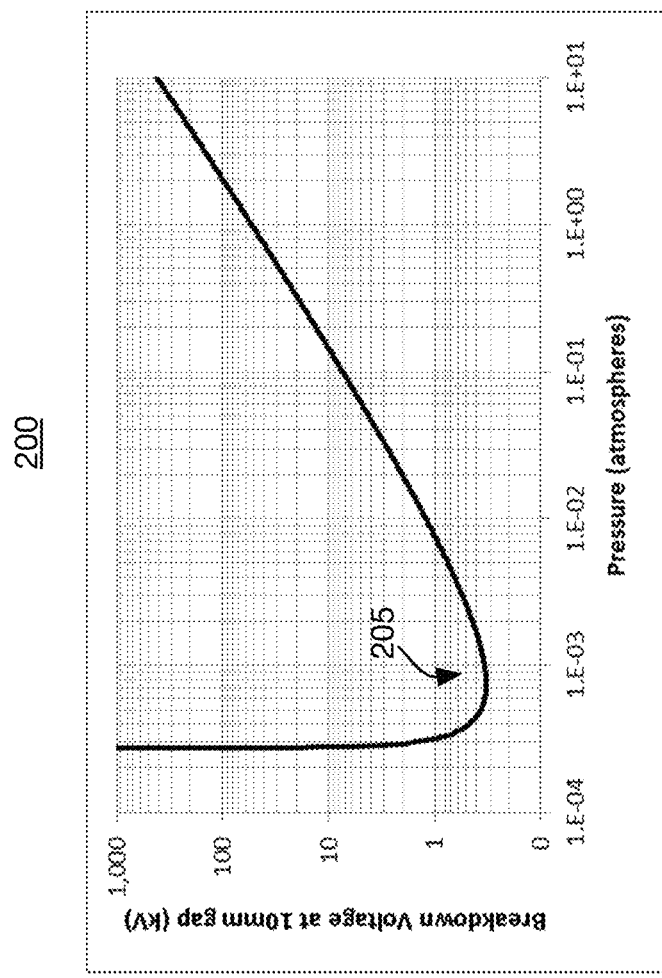
FIG. 2 is an exemplary plot of a relationship between breakdown voltage and pressure.

Referring also to FIG. 2, an example of an ideal Paschen curve 200, which illustrates the relationship between breakdown voltage and pressure for electrodes with a 10 mm electrode gap in air, is shown. At standard pressure (one atmosphere), a 1 cm electrode gap with spherically shaped electrodes and no field enhancement has a breakdown voltage of approximately 50 kilovolts (kV). If the air pressure is increased to two atmospheres, the breakdown voltage increases to about 100 kV. If the pressure is decreased to half an atmosphere, the breakdown voltage decreases to just under 30 kV. The breakdown voltage continues to decrease with decreasing pressure until the Paschen minimum 205, which is the minimum breakdown voltage for the range of pressures shown on the curve 200, is reached. For the example shown in FIG. 2, the Paschen minimum 205 occurs around a vacuum level (pressure) of about $7.5\times10^{-4}$ atmospheres (about 0.57 Torr). The breakdown voltage at the Paschen minimum 205 is about 0.3 kV. Continuing to pull a vacuum level deeper than the Paschen minimum 205 (pulling a vacuum to a lower pressure) results in an increase in the breakdown voltage. As discussed above, vacuum interrupters operate far to the left of the Paschen minimum, in the $10^{-8}$ atmosphere, or $10^{-5}$ Torr, range, where field emission and other aspects determine breakdown strength. A pressure in this range is referred to as the deep operating pressure.

Referring again to FIGS. 1A and 1B, if the vessel 102 leaks, the pressure in the vessel 102 increases, approaching and passing through the Paschen minimum for the vacuum interrupter 100 while leaking up to atmospheric pressure. This loss of the vacuum in the vessel 102 (the increase in the pressure of the evacuated space 104 from the deep operating pressure to pressures near and above the Paschen minimum) may cause failure of the vacuum interrupter 100, regardless of whether the contacts 110, 114 are open or closed. For example, if the contacts 110, 114 are open when the vacuum in the vessel 102 is lost, or are opened after the vacuum in the vessel 102 is lost, an arc may form between the contacts 110, 114. Additionally, when the vessel 102 leaks, oxygen flows into the vessel 102 and can cause oxidation of the contacts 110, 114 and a corresponding increase in the contact resistance and the production of additional heat when carrying current. Thus, the leaking of the vessel 102 may lead to a thermal runaway condition and/or a loss of voltage and current isolation across the open contacts 110, 114.

It can be challenging to detect the loss of the vacuum in the vessel 102 mechanically. For example, a mechanical vacuum gauge may not be precise enough to detect loss of the vacuum in the vessel 102 (or the increase in the pressure of the evacuated space 104) when the vacuum interrupter 100 is in use. A mechanical vacuum gauge attached to the vacuum interrupter 100 with the evacuated space 104 having a vacuum level of $3\times10^{-8}$ atmospheres, or $2\times10^{-5}$ Torr, would read −101.33 kilopascals (kPa), (−14.696 psi) relative to standard pressure. At this deep operating pressure, the vacuum interrupter 100 works properly. At and near the Paschen minimum, the vacuum level is not sufficient to provide good electrical properties of the vacuum interrupter, but, due to the rapidly changing breakdown voltage relative to pressure changes near the Paschen minimum, the level of the vacuum read from a mechanical gauge at or near the Paschen minimum can be nearly indistinguishable from that of the deep operating pressure. For example, a mechanical vacuum gauge reading a pressure at the Paschen minimum, which may be about $7.5\times10^{-4}$ atmospheres, or 0.57 Torr, would read −101.25 kPa (−14.685 psi). Voltage withstand performance may be affected at pressures that are near the Paschen minimum, for example, around $2.7\times10^{-4}$ atmospheres, or 0.21 Torr. At this level, a mechanical gauge would read −101.30 kPa (−14.692 psi). Given other variability in the system that can occur during operation, it can be challenging to differentiate the pressure readings from the mechanical gauge at or near the Paschen minimum from the deep operating pressure. Thus, the mechanical vacuum gauge may fail to detect the loss of the vacuum in the vessel 102 (the increase in pressure of the evacuated space 104).

It can also be difficult to detect the loss of vacuum with a capacitance measurement. Capacitance is proportional to the dielectric constant. The dielectric constant for an ideal vacuum is 1, by definition. For air at standard temperature and pressure the dielectric constant is about 1.0006. The ability to differentiate between the close values can be difficult under operating conditions because, for example, of other system variations that can occur during operation of the vacuum interrupter 100.

However, small changes in pressure can cause large changes in the indication of impedance measured by the sensor 130, and the vacuum sensing system 131 may therefore detect small changes in the pressure of the evacuated space 104 by changes in the impedance.

The sensor 130 of the vacuum sensing system 131 provides a signal that is related to impedance of a region in the vacuum interrupter 100 to the controller 140. The controller 140 communicates with the sensor 130 through an interface 146. The interface 146 may include electrically conductive wires, leads, or any other connection. The controller 140 may include an electronic processor 136, an electronic storage 137, and a transceiver 138. The electronic storage 137 stores instructions, perhaps in the form of a computer program, that, when executed cause the electronic processor 136 to process the signal to determine a condition of the evacuated space 104. For example, the signal may be processed to determine the impedance of the sensor 130 and to compare that impedance to a previous impedance to detect whether the impedance changed. An increase in the impedance of the sensor may indicate that the vessel 102 has lost vacuum (the pressure of the evacuated space 104 has increased).

The transceiver 138 provides an indication of the condition of the evacuated space 104 to a receiver or processor that is located remote from the vacuum interrupter 100, for example, in another part of a power system (not shown) that includes the vacuum interrupter 100 or at an operator's station (not shown). When the indication of the condition of the space 104 shows that the pressure of the space 104 has increased beyond a threshold leave, the transceiver 138 may provide a signal to, for example, the operator's station that is sufficient to remove the vacuum interrupter 100, or a switchgear that includes the vacuum interrupter 100, from service. The controller 140 includes or is powered by a power source 139 that provides power to the controller 140 regardless of whether the contacts 110, 114 are in the open or closed position. The controller 140 also may include devices for exciting or characterizing the sensor 130, such as a constant current source and/or a voltage meter.

Figure 3:
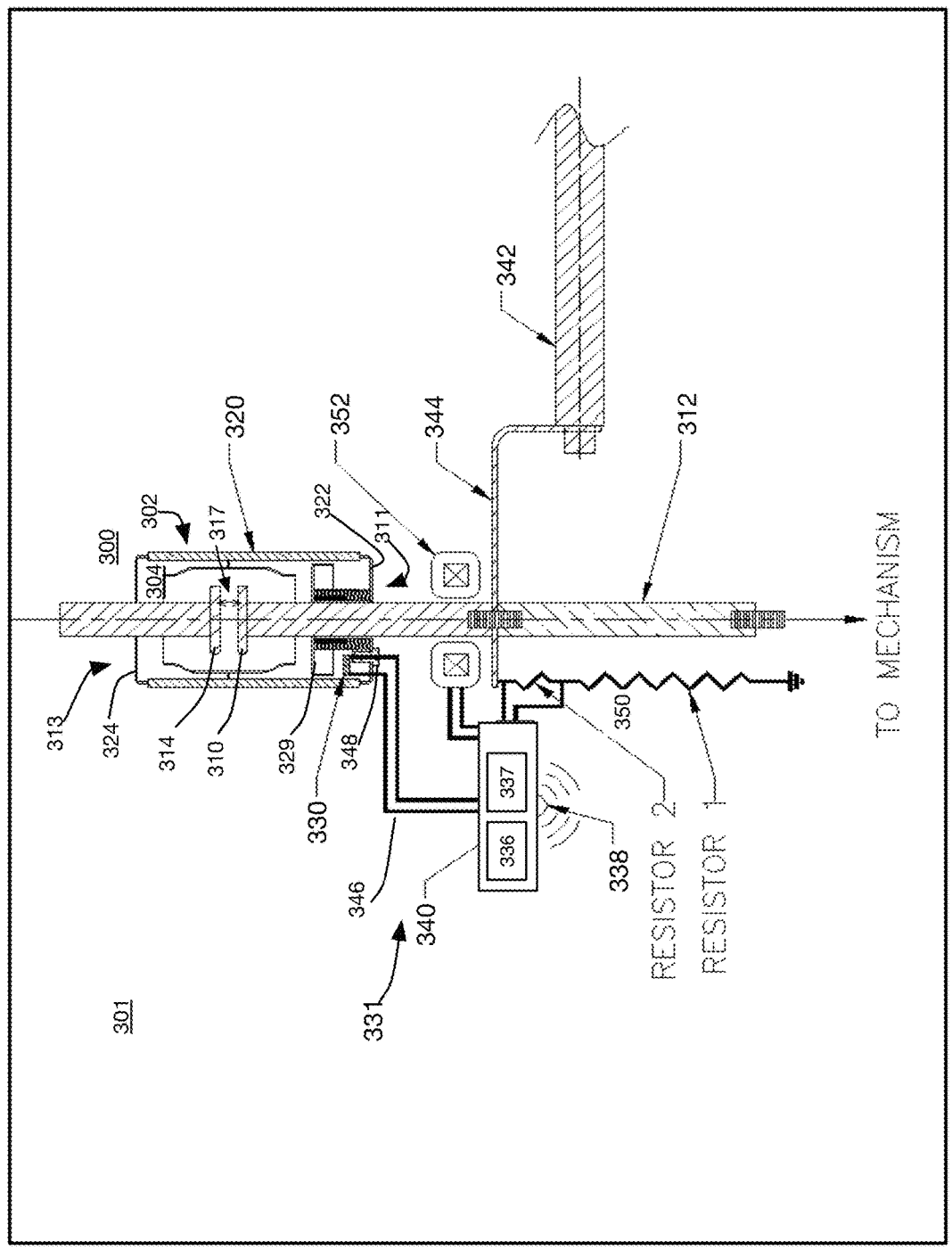
FIG. 3 is a side-cross sectional view of another exemplary vacuum interrupter and a vacuum sensing system.

FIG. 3 shows an exemplary implementation of a switchgear device 301 with a vacuum sensing system 331. The switchgear device 301 includes a vacuum interrupter 300 with a movable contact 310 that moves relative to a stationary contact 314. The vacuum interrupter 300 is opened and closed by moving the movable contact 310 via an actuation rod 312 by a mechanism (not shown). The vacuum interrupter 300 is shown in the open position, with the movable contact 310 and the stationary contact 314 separated by a gap 317.

The vacuum interrupter 300 includes a vessel 302 that encloses the contacts 310, 314 and is designed to maintain a vacuum seal. Air is removed from the vessel 302, leaving an evacuated space 304. After the air is evacuated, the pressure of the evacuated space 304 may be, for example, on the order of $10^{-8}$ atmosphere, or $10^{-5}$ Torr. The vessel 302 includes an electrical insulator 320 and endcaps 322, 324. The vacuum interrupter 300 also includes a shield 329 that extends radially outward from the longitudinal axis of the vacuum interrupter and is between the contacts 310, 314 and the sensor 330. The shield 329 protects the sensor 330 from arcing that may occur between the contacts 310, 314.

The vacuum sensing system 331 includes a sensor 330 and a controller 340, which is external to the vacuum interrupter 300. The controller 340 includes an electronic processor 336, an electronic storage 337, and a wireless transceiver 338. Current flow through the vacuum interrupter 300 may be through a conductor 342 that is connected to the vacuum interrupter 300 by a flexible lead 344, or other current exchanges as are known in the art.

The sensor 330 measures an impedance, or provides an indication of impedance, and is mounted inside the vacuum interrupter 300. The sensor 330 produces a signal that includes values or data representing the measured impedance, and provides the signal to the controller 340. The electronic processor 336 of the controller 340 analyzes the signal to determine the condition of the evacuated space 304.

The sensor 330 may receive data from and provide data, including the signal, to the controller 340 through leads 346. One or more of the leads 346 may pass through an electrically insulated feed-through 348 in a wall of the vessel 302. The insulated feed-through 348 is shaped to fit an opening in the wall of the vessel 302 and to seal the opening. The insulated feed-through 348 receives and holds at least one of the leads 346. The insulated feed-through 348 holds the leads 346, allowing the leads 346 to pass through the vessel 302 (through the endcap 322 in the example of FIG. 3) while still maintaining the vacuum seal of the vessel 302. More than one lead 346 may pass through one or more of the feed-through 348.

The controller 340 and its components, including the electronic processor 336, may be powered by the current flow that flows through the vacuum interrupter 300 when the contacts 310, 314 are closed via a current transformer 352 that is positioned around the current path. Alternately, the electronic processor 336 may be powered by a voltage divider 350, which includes Resistor 1 and Resistor 2. The value of Resistor 1 is high compared to Resistor 2. For example, Resistor 1 may be on the order of 100 MegaOhms (MΩ), compared to that of Resistor 2, which may be on the order of 100 kΩ. Either Resistor 1 or Resistor 2, or both Resistor 1 and Resistor 2, may be mounted inside the actuation rod 312, as shown in U.S. Pat. No. 7,473,863, which is incorporated by reference herein in its entirety. The voltage divider 350 provides power to the controller 340 even when the contacts 310, 314 are open. By using a combination of these powering techniques, power to the controller 340 may be maintained whether the contacts 310, 314 are open or closed. Therefore, the state or condition of the evacuated space 304 may be monitored regardless of whether the contacts 310, 314 are open or closed.

It is also understood that although the electronic processor 336 is shown powered by the current transformer 352 and the voltage divider 350, the electronic processor 336 may also be powered by only one of these. Alternately, a voltage divider could also be from the moving end 311 to a stationary end 313 of the vacuum interrupter 300 to provide power when the contacts 310, 314 are open but the stationary end 313 is energized. Other techniques of energy harvesting are also possible, and any of these could be used instead of, or in addition to, the examples already mentioned. For example, a battery could also or alternatively be used to provide power to the controller 340.

In the implementation shown in FIG. 3, the electronic processor 336 is at high voltage, near the voltage of a moving end 311 of the vacuum interrupter 300, and the state of the evacuated space 304 is transmitted wirelessly by the wireless transceiver 338 to a receiver (not shown) mounted elsewhere in the switchgear or power system (not shown). The wireless transmission may be by visible or invisible light, for example, via a light emitting diode, or may be via other wireless transmission methods, for example wireless Ethernet protocols, Bluetooth wireless communications protocol, fixed radio frequency protocols, and/or spread spectrum radio protocols. Other communications methods may be used as well.

Figure 4:
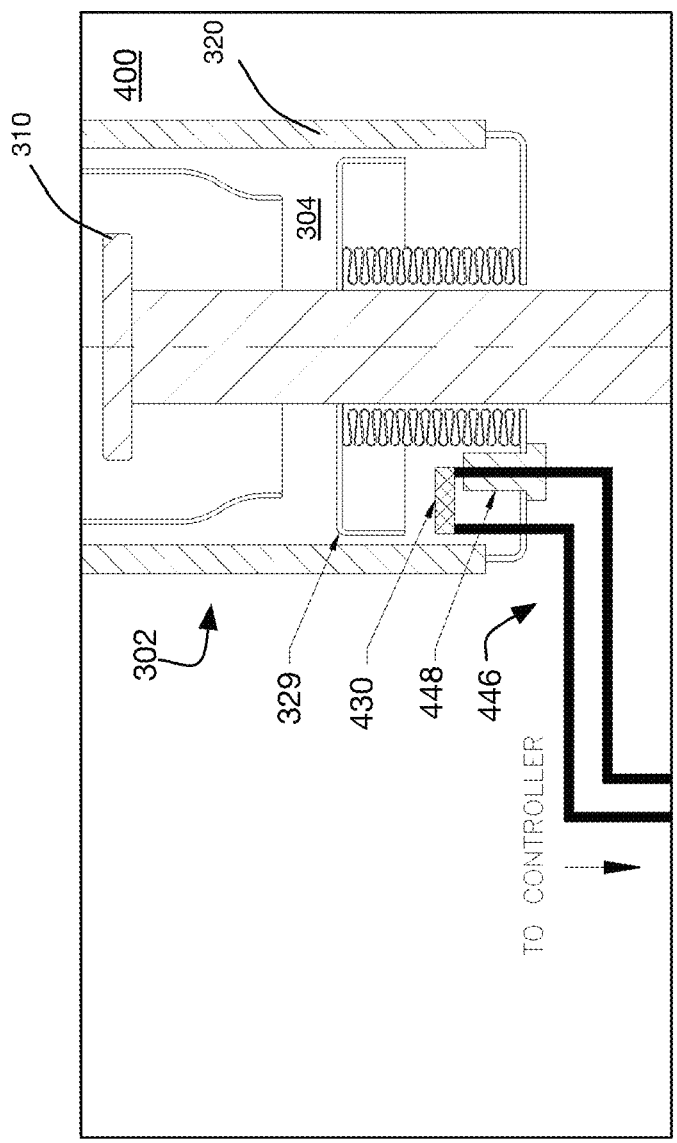
FIGS. 4-10 are partial side cross-sectional views of exemplary sensor elements installed in a vacuum interrupter.

FIG. 4 is a partial side cross-sectional view of an exemplary sensor 430 installed in a vacuum interrupter 400. The vacuum interrupter 400 is similar to the vacuum interrupter 300, and the sensor 430 may be used as the sensor 330. Thus, the vacuum interrupter 400 is described with reference to FIG. 3.

In the implementation shown in FIG. 4, the sensor 430 is a sensing filament placed inside the vessel 302. The filament 430 is connected to the controller 340 (not shown) through leads 446, one of which passes through an electrically insulating feed-though 448 that is positioned in a wall of the vessel 302. The insulating feed-through 448 allows the leads 446 to pass through a wall of the vessel 302 without disturbing the vacuum seal of the vessel 302.

The filament 430 may be a wire or a ribbon of a metal, for example, tungsten or zirconium, which changes resistivity (and therefore resistance), significantly depending on whether the metal is pure or oxidized, either through surface oxidation or through bulk oxidation, or a combination thereof. For example, the electrical resistivity of pure zirconium is $4 \times 10^{-5}$ ohm·cm, but once oxidized, the resistivity is about $10^7$ ohm·cm, more than ten orders of magnitude greater.

When a small leak occurs in the vessel 302, even when the pressure in the vessel 302 is near the Paschen minimum, air leaks into the vessel 302, oxidizing the filament 430. The resistance of the filament 430 increases as a result of oxidation and this increase in resistance is measurable by the controller 340. The controller 340 may measure the resistance of the filament 430 by, for example, passing a current of a known amount through the filament 430 and measuring the voltage across the filament 430 that occurs due to the current. In this example, to determine an indication of impedance, the electronic processor 336 divides the measured voltage by the known current to determine the resistance of the filament 430. The controller 340 may measure the resistance of the filament in any other known manner.

Furthermore, the microstructure of the filament 430 also may be adjusted through porosity, grain boundary manipulation, or surface roughness to enhance and/or increase the effective surface area available for interaction with the oxidizing agent upon a vacuum leak condition. By increasing the effective surface area of the filament 430, the change in resistance may occur more quickly, allowing the change in resistance (and therefore the increase in pressure in the vessel 302) to also be measured more quickly. In some implementations, depending on the vacuum loss and the amount of current flowing through the filament 430, the filament 430 may fuse, resulting in a near-infinite resistance.

Figure 5:
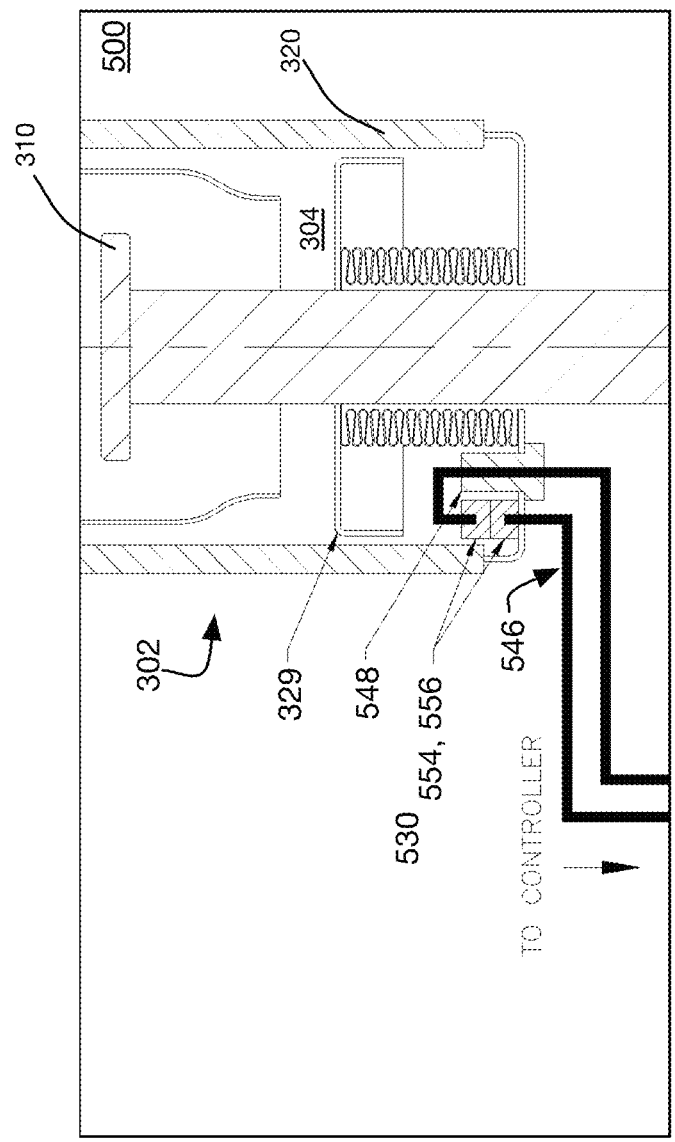

FIG. 5 shows an exemplary sensor 530 installed in a vacuum interrupter 500. The vacuum interrupter 500 is similar to the vacuum interrupter 300, except for details regarding the sensor 530. Thus, the vacuum interrupter 500 is described with additional reference to FIG. 3. The sensor 530 may be used as the sensor 330.

The sensor 530 includes a pair of contacts 554, 556 that are placed inside the vessel 302. The contacts 554, 556 may be made out of, for example, a copper alloy, or a tungsten or zirconium alloy. The contacts 554, 556 are not the primary interrupting contacts 310, 314, and the pair of contacts 554, 556 are always closed (in physical contact with each other). The contacts 554, 556 are not, for example, brazed together, and could be separated if a bellows, or other actuation means, were designed into the interrupter 500. However, the contacts 554, 556 are intended to be kept closed and in physical contact with each other. A small spring (not shown) may be used to apply contact pressure to the contacts 554, 556 to maintain the physical contact between the contact 554 and the contact 556.

If the vessel 302 leaks, oxygen enters the vessel and the pressure in the vessel 302 increases. The contacts 554, 556 oxidize in the presence of the oxygen, leading to an increase in the contact resistance between the contacts 554, 556. Thus, an increase in the contact resistance provides an indication of the state or condition of the evacuated space 304. To test for an increase in the contact resistance, the controller 340 (FIG. 3) may send a small amount of current through the contacts 554, 556 continuously, at a known temporal interval, or in response to operator intervention. If a leak occurs in the vessel 302, even a small leak, the contact resistance between the contacts 554, 556 increases as a result of oxidation, resulting in a measurable change in contact resistance. Similarly to the filament 430 of FIG. 4, the microstructure of the material of the contacts 554, 556 may be adjusted through porosity, grain boundary manipulation, or surface roughness to enhance and/or increase the effective surface area available for interaction with the oxidizing agent, upon a vacuum leak condition.

Figure 6:
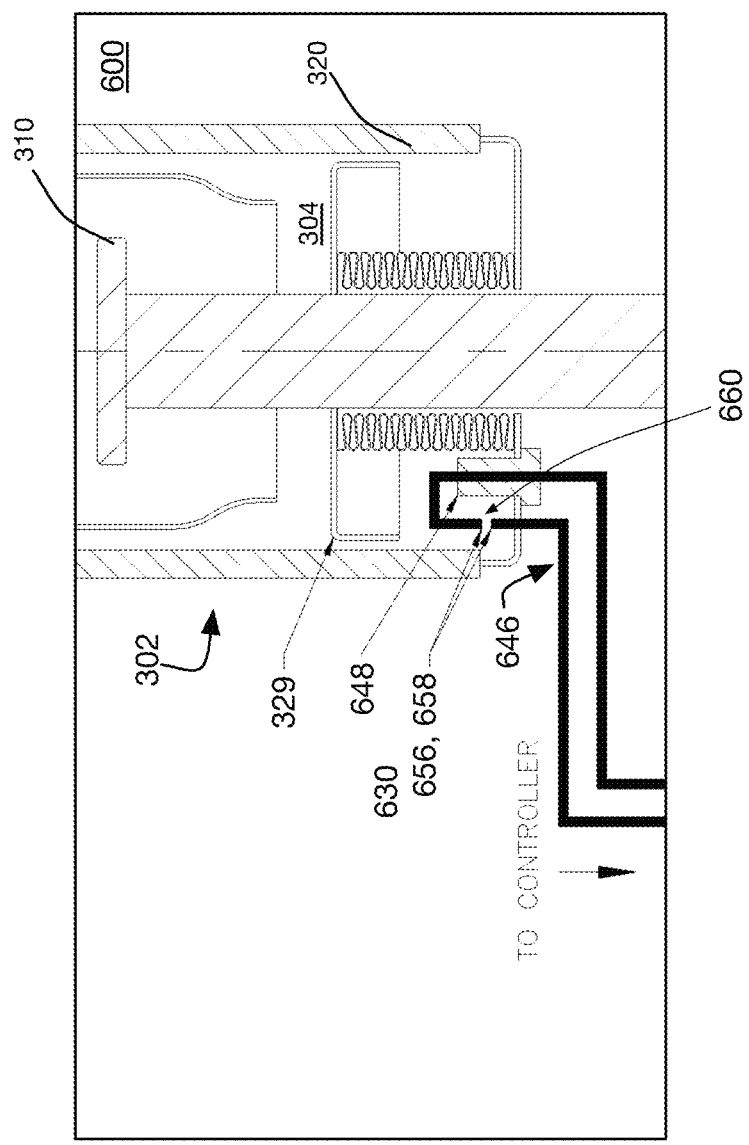

FIG. 6 shows an exemplary sensor 630 installed in a vacuum interrupter 600. The vacuum interrupter 600 is similar to the vacuum interrupter 300, except for details regarding the sensor 630. Thus, the vacuum interrupter 600 is described with additional reference to FIG. 3. The sensor 630 may be used as the sensor 330.

The sensor 630 includes a small pair of contacts 656, 658 placed inside the vessel 302 and connected to the controller 340 by leads 646, at least one of which passes through an electrically insulating feed-through 648 that is in a wall of the vessel 302. The contacts 656, 658 are separate from and in addition to the main interrupting contacts 310, 314. The contacts 656, 658 are held open, and are physically separated from each other by a gap 660. The sensor 630 may be used to measure an indication of resistance and an indication of the condition or state of the evacuated space 304 in the vessel 302. However, rather than measuring resistance, when the sensing device 630 is used, the controller 340 measures withstand voltage across the gap 660 between the contacts 656, 658. To measure the withstand voltage across the gap 660, the controller 340 applies a voltage across the contacts 656, 658.

If the vacuum level in the vessel 302 is near or approaches the Paschen minimum, then the gap 660 will break down and a spark or arc forms across the gap 660. Because the size of the gap 660 is smaller than the gap 317 (FIG. 3) between the contacts 310, 314 in the open position, the voltage difference required for breakdown across the gap 660 is lower than the voltage difference for breakdown between the primary vacuum contacts 310, 314. As such, the gap 660 may be tuned (increased or decreased) so as to produce a failure at a deeper vacuum (lower pressure) than the primary contacts 310, 314, and an indication of a leak in the vessel 302 may be provided by the controller 340 sooner and without causing dielectric failures elsewhere in the vacuum interrupter 300 or power system that includes the vacuum interrupter 100.

In some implementations, the gap 660 may be about one-third to one-tenth the size of the gap 317. For example, the gap 660 may less than 2 millimeters (mm), and the gap 317 may be on the order of 6 mm to 16 mm. Alternately, a high geometry field enhancement may also be used to lower the breakdown voltage of sensing gap 660.

Alternately or additionally, leakage current could be measured across the gap 660. If a small vacuum leak occurs, the leakage current value would also increase. Thus, a measurement by the controller 340 that the leakage current has increased is an indication of loss of the vacuum in the vessel 302 (or an increase in pressure of the evacuated space 304).

The implementations of FIGS. 4-6 connect the sensors 430, 530, 630, respectively, to the controller 340 with wires or leads 446, 546, 646 that pass through a wall of the vessel 302. If the wires pass through one of the vacuum interrupter endcaps 322, 324, then the wires must be isolated from each other. One of the wires may be directly affixed to the endcap 322, and held at the voltage potential of the endcap 322. However, at least one wire passes through the insulating feed-through 448, 548, 648, respectively, which is mounted to the endcap 322. It is understood that one or both wires may go through the feed-through 448, 548, 648, so long as the wires are electrically isolated from each other.

Figure 7:
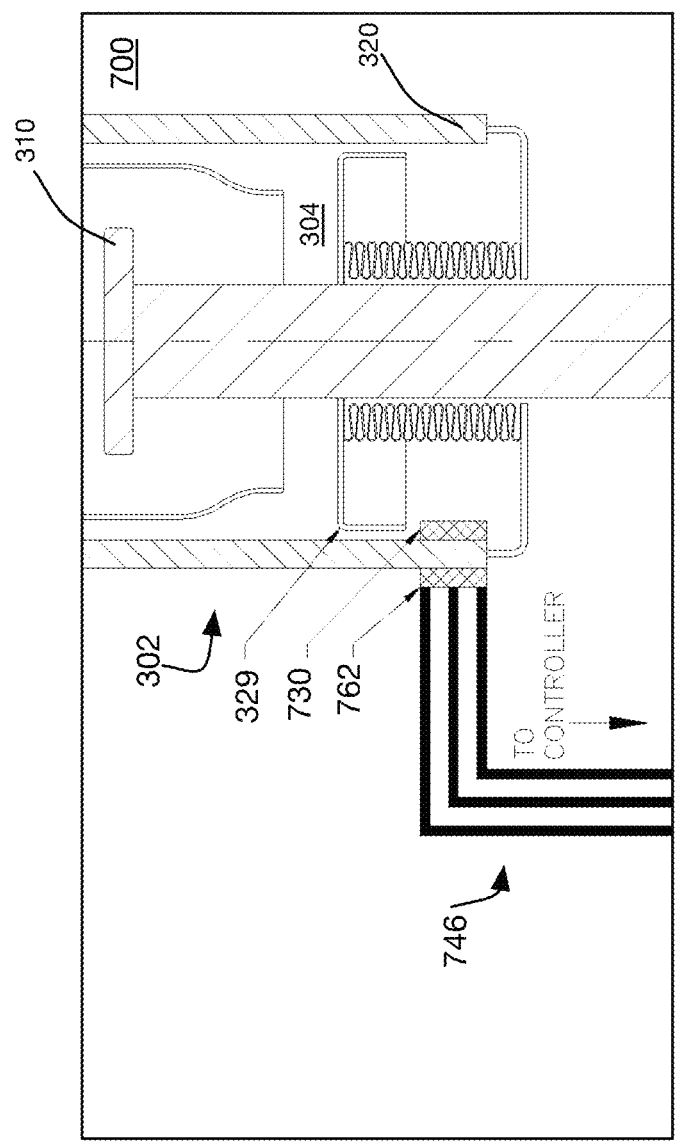

FIG. 7 shows an exemplary sensor 730 installed in a vacuum interrupter 700. The vacuum interrupter 700 is similar to the vacuum interrupter 300, except for details regarding the sensor 730 and the lack of a feed-through passing through a wall of the vessel 302. Thus, the vacuum interrupter 700 is described with additional reference to FIG. 3. The sensor 730 may be used as the sensor 330.

The sensor 730 includes a conductivity probe 762 and a sensor 730 mounted inside the ceramic insulator 320 of the vacuum vessel 302. The sensor 730 may be, for example, a filament or ribbon that is at least partially metallic or electrically conductive and experiences oxidation in the presence of an oxidizing agent, such as air. The conductivity probe 762 is placed outside the ceramic insulator 320 (and external to the vacuum interrupter 300) after the vacuum interrupter 300 has been brazed. The conductivity probe 762 is coupled to the controller 340 through leads 746. In the example shown, the leads 746 include an excitation lead, a common lead, and a non-common lead.

As discussed above, if the vacuum interrupter 700 leaks, the pressure in the vessel 302 increases. Additionally, the leak allows air and other fluids to enter the vessel 302. The air and/or other fluids causes oxidation of the sensor 730, increasing the resistance of the sensor 730. Therefore, an increase in the resistance of the sensor 730 may indicate that the pressure is increasing in the evacuated space 304.

The conductivity probe 762 is used to measure the conductivity or the electrical resistance of the sensor 730. The conductivity probe 762 generates magnetic fields, either with high frequency alternating current (AC) signals (such as, for example, 1 kHz-1 MHz) or by pulsing direct current (DC) signals. The magnetic fields generated by the conductivity probe 762 generate eddy currents in nearby metals, including the sensor 730. The conductivity probe 762 measures the generated magnetic fields, which are affected by eddy currents in neighboring metals. For example, the electrical resistance of the metal reduces the amplitude of the eddy currents. Thus, the amplitudes of the generated magnetic fields measured by the conductivity probe 762 are correlated with the resistance of the sensor 730. As such, the conductivity probe 762 may measure the electrical resistance of the sensor 730 from the generated eddy currents.

Furthermore, in contrast to the implementations shown in FIGS. 4-6, the sensing device 730 does not require an additional vacuum seal, such as the insulating feed-throughs 348, 448, 548, and 648. Thus, the resistance of the sensor 730 may be measured without placing additional vacuum seals through the walls of the vessel 302.

Other implementations are within the scope of the claims. For example, other configurations of the shield 129 are possible. In some implementations, the shield 129 may extend vertically along the longitudinal axis 103 and between the sensor 130 and the contacts 110, 114 instead of extending radially from the longitudinal axis 103.

In the implementations discussed above, the sensors 130, 330, 330, 430, 530, 630, 730 are positioned near the endcap 122 or 322 that is closest to the movable rod 112, 312. In other implementations, the sensors may be located closer to the endcap 124, 324.

The current transformer 352 and the voltage divider 350 may be used with the vacuum interrupter 100 to provide power to the controller 140 and its components.

The sensors 430, 530, 630, 730 may be used with other vacuum interrupters. For example, any of the sensors 430, 530, 630, 730 may be used in the vacuum interrupter 100 as the sensor 130 and coupled to the controller 140.

The electronic storage 137 of the controller 140 and the electronic storage 337 of the controller 340 may be volatile memory, such as RAM. In some implementations, and the electronic storage 137, 337 may include both non-volatile and volatile portions or components. The electronic processors 136, 336 may be one or more processors suitable for the execution of a computer program such as a general or special purpose microprocessor, and any one or more processors of any kind of digital computer. Generally, a processor receives instructions and data from a read-only memory or a random access memory or both.

The electronic processors 136, 336 may be any type of electronic processor and may be more than one electronic processor. The electronic storage 137, 337 stores instructions, perhaps as a computer program, that, when executed, cause the electronic processor 136, 336 to communicate with other components in the controller 140, 340 and/or the sensor 130, 330. For example, the instructions may be instructions to provide a current through the sensor 130, 330 and measure a resulting voltage. The electronic storage 137, 337 may store a digital representation of a signal generated by the sensor 130, 330, and of signals generated by the sensor 130, 330 in the past (at an earlier time). The electronic storage 137, 337 also may store threshold values to which to compare the signal from the sensor 130, 330, or the processed signal.

In some implementations, a fully digital processor may not be required. For example, the sensor 130, 330 may be a filament and the current flow through the filament powers an LED. In this implementation, the processor 136, 336, may be a photodiode with a threshold light detection level.

Figure 8:
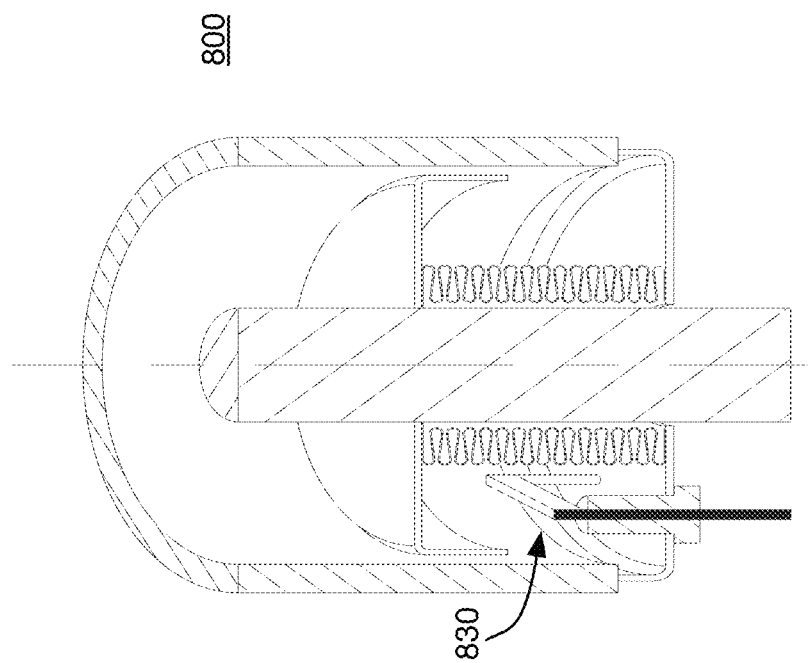

Additionally, although the sensor is shown schematically in the radial or axial orientations, the sensor could be in other orientations as well, for example, in coaxial or circumferential orientations. For instance, FIG. 8 shows a partial side cross-sectional view of an exemplary sensor 830 installed in a vacuum interrupter 800. The sensor 830 is a sensing filament similar in function to sensor 430, but the sensor 830 is placed in a circumferential orientation rather than in a radial orientation.

Figure 9:
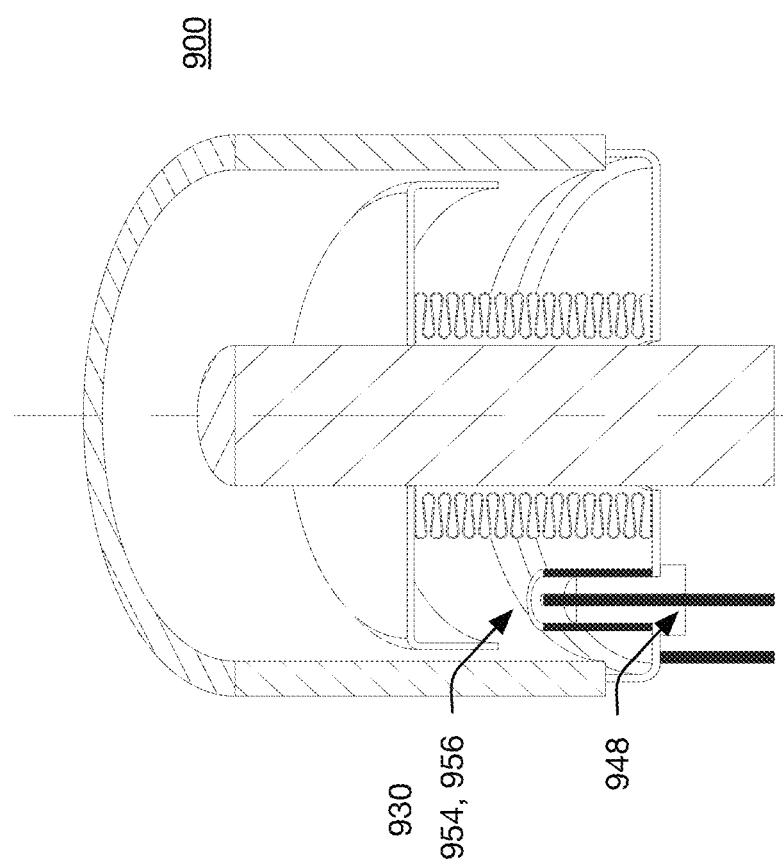

In another example, FIG. 9 shows a partial side cross-sectional view of an exemplary sensor 930 installed in a vacuum interrupter 900. The vacuum interrupter 900 is similar to that of vacuum interrupter 500, however the sensing contacts 954, 956 are placed coaxially with that of insulating feed-through 948.

Furthermore, in some implementations, only one contact may be added, and may be paired with pre-existing portions of the vacuum interrupter, for instance, an endcap or a shield. Further, although the contacts are shown as connected to the controller through feed-throughs in the endcap 322, the feed-throughs may also be through other components of the vacuum interrupter 100, 300 or the vessel 102, 302, for instance, the ceramic insulator 120, 320.

Figure 10:
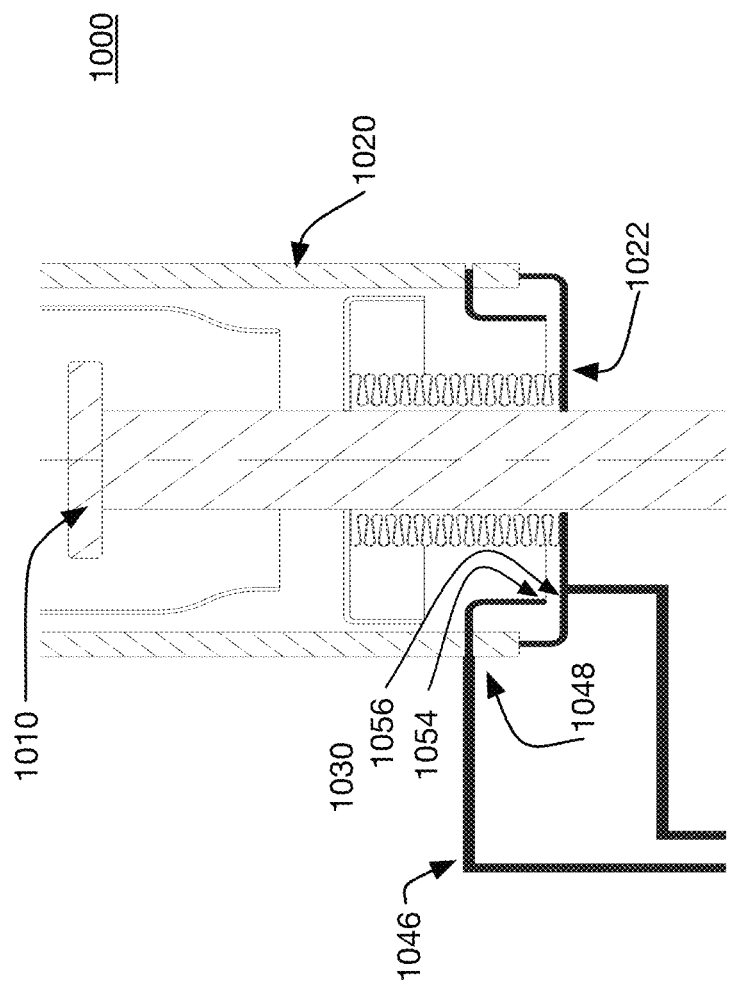

For instance, FIG. 10 shows a partial cross-sectional view of sensor 1030 installed in a vacuum interrupter 1000 similar to that of vacuum interrupter 500, however the sensing contacts 1054, 1056 are placed coaxially with that of an insulator 1020 and a movable contact 1010. In the implementation of FIG. 10, the contact 1054 is paired with an endcap 1022 of the vacuum interrupter 1000, with the endcap 1022 acting as the contact 1056. Insulating feed-through 1048, rather than being through endcap 1022 is coaxial with insulator 1020 and is of substantially the same inside and outside diameters as insulator 1020, allowing an isolated signal 1046 to pass between insulating feed-through 1048 and insulator 1020.

In implementations in which a resistance or a leakage current or a change in resistance or leakage current of a sensor is monitored or tracked, other parameters may also or alternatively be monitored or tracked. For example, temperature of the sensor or a region in the vicinity of the sensor may be tracked. A change in resistance of an electrically conductive element causes a corresponding change in the temperature of the element when current flows through the element. For example, for a given amount of current passing through an electrically conductive element, an increase in resistance of the element causes the element to produce more heat when the current flows in the element.

Thus, in some implementations, the temperature of electrically conductive components in the vacuum interrupter 100, 300 can be tracked and/or monitored as an indirect measurement of the pressure in the vessel 102, 302. For example, the temperature of the primary (or main) contacts 110, 114 or 310, 314 may tracked in addition to or instead of the temperature of the sensor, and the temperature of the primary contacts may be compared with a known reference temperature for the current carrying and ambient conditions. In implementations in which the temperature is tracked or monitored, the sensor may be, for example, a thermocouple or any other sensor that measures temperature, such as a resistance temperature device or a thermistor device.

Figure 11:
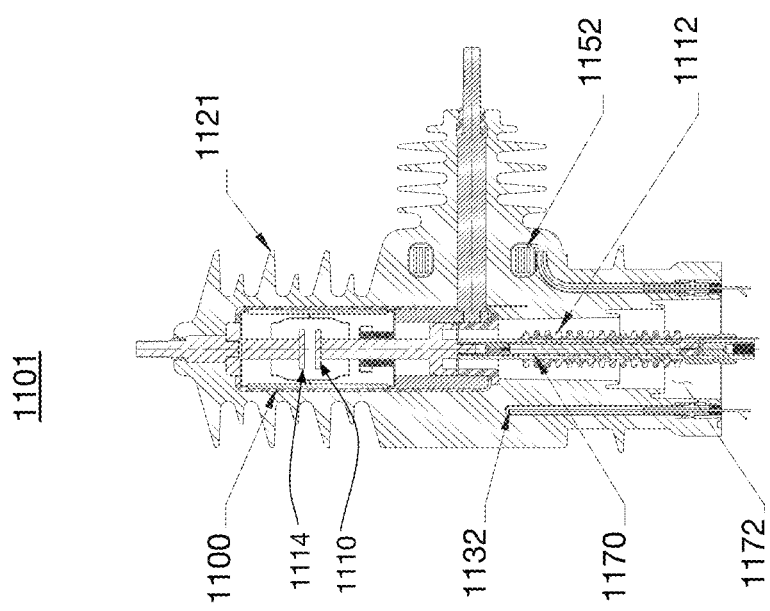
FIG. 11 is a cross-sectional view of an exemplary sensor element installed in an insulation of a vacuum interrupter.

FIG. 11 shows an example of such a sensor. FIG. 11 is a cross-sectional view of a switchgear device with a vacuum interrupter 1100 that has been encapsulated in solid insulation 1121, as shown in, for instance U.S. Pat. Nos. 5,917,167 and 6,760,206, which are incorporated by reference herein in their entirety. The switchgear device 1101 may contain many of the elements that are similar to those of the switchgear device 301, including a current sensor 1152, and an actuating rod 1112 containing a voltage sensor 1170, which includes a resistor R1. A resistor R2 is on the low voltage side of this system, in the mechanism (not shown) or the control system (not shown). The switchgear device 1101 also includes a voltage sensor 1170 and an operating cavity 1172. A thermal sensor 1132, which may be a thermocouple, a thermistor, or any other sensor configured to measure temperature, has also been embedded in the solid insulation 1121 that surrounds the device 1101. The thermal sensor 1132 is placed in proximity to the vacuum interrupter 1100.

Figure 12:
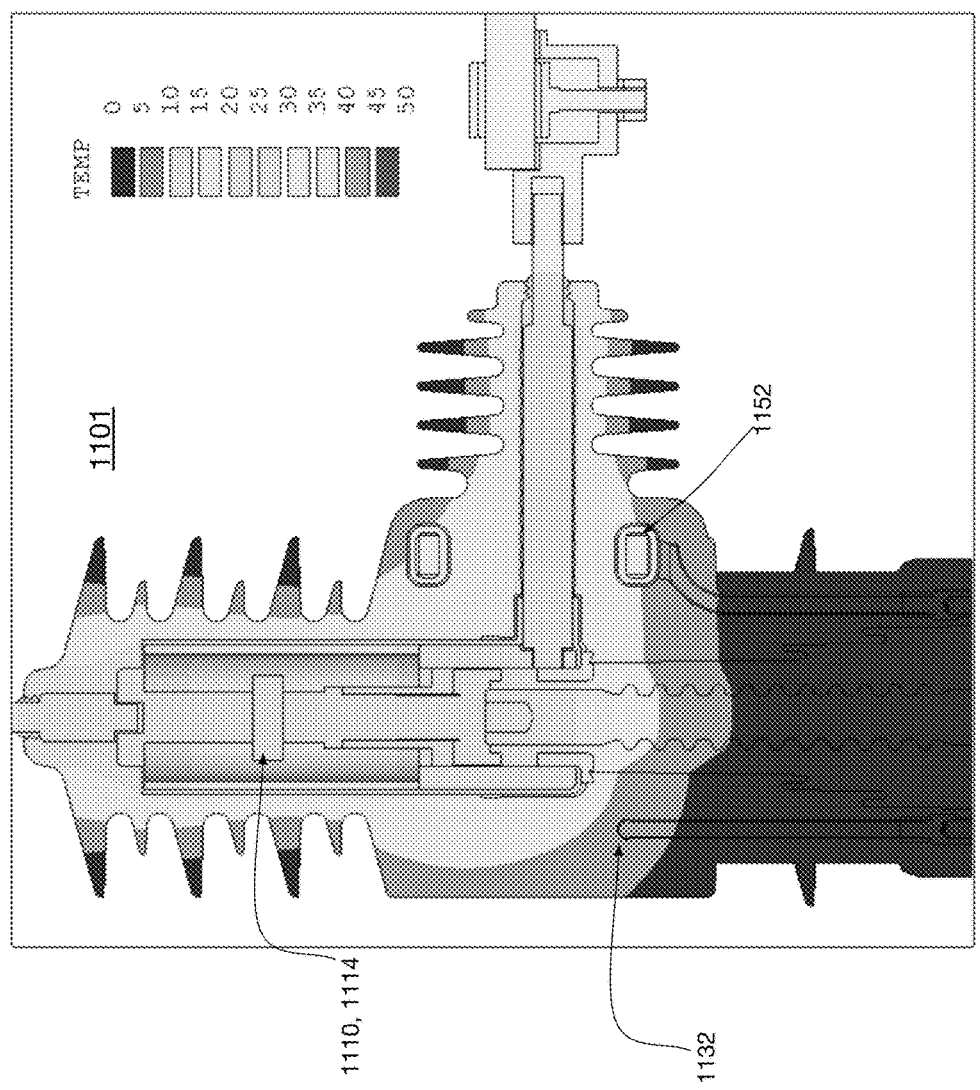
FIG. 12 is an exemplary thermal gradient of heat rise as a function of current flowing through a switchgear device.

FIG. 12 shows an exemplary plot of an expected thermal gradient in Celsius (C) of the heat rise as a function of current flowing through the switchgear device 1101. This heat is generated by power loss and is a function of the impedance of the switchgear device 1101 and the square of the current flowing through the device. The current flow is measured by the current sensor 1152, thus, the temperature at any point in the switchgear device 1101, for instance, the location of thermal sensor 1132, can be predicted. By comparing the output of the thermal sensor 1132 to that of a sensor measuring the ambient temperature elsewhere in the system, thermal sensor 1132 can also measure this heat rise. The predicted value based on current sensor 1152 can be compared to the measured value from the sensor 1132. If the temperature measured by the sensor 1132 is hotter than the expected value by a predetermined limit, for instance 10C, then oxidation of the vacuum interrupter contacts 1110, 1114 from vacuum loss, or other faults in the system, may be the cause, and the system can react accordingly before damage occurs. Alternately, rather than comparing to a calculated expected heat rise, in a three-phase system, the output of three sensors 1132 may be compared to each other. If one of the three sensors reads hotter than the other two by a predetermined amount, then, again, the system can react accordingly before damage occurs.

It is appreciated that those skilled in the art may recognize that the proximity of the sensor 1132 to the vacuum interrupter 1100 may affect its sensing accuracy. Alternately, electrical stress between sensor 1132 and 1100 may increase as the two get closer. These two may be balanced to allow proper sensor accuracy without placing undue electrical stress on the system.

The discussion of FIGS. 11 and 12 assumes a solid dielectric system. The temperatures of other insulation systems, for instance mineral oil or SF6 may be used and monitored as well.

Alternately, a thermal sensor, such as the thermal sensor 1132, could also be used to measure a temperature near any of the vacuum interrupters shown in FIGS. 4-9. The resulting measured data may be used to make a decision assessing the impedance of those sensors or the vacuum level accordingly.

Monitoring of the resistance of filaments, ribbons, contact sets, and other similar techniques includes monitoring of the real and/or imaginary parts of the impedance. Likewise, it is to be understood that control voltages or currents or waveforms may be of any number of frequencies and/or modulated signals to best monitor and interpret the physical conditions of the vacuum level. Material/electrical modulation combinations may be optimized depending upon the application and physical product implementation.

What is claimed is:
1. A sensing system of a vacuum interrupter, the sensing system comprising:
a sensor comprising a material that oxidizes in the presence of air and is at least partially positioned in an evacuated space of a vacuum interrupter, the sensor being configured to produce an indication of impedance of the material, wherein the material is initially non-oxidized and becomes oxidized in response to air entering the evacuated space, and the impedance of the material depends on whether the material is non-oxidized or oxidized; and a control system coupled to the sensor, the control system comprising an electronic processor and an electronic storage that stores instructions that, when executed, cause the electronic processor to:
   access an indication of impedance produced by the sensor,
   determine a measure of impedance of the material of the sensor based on the accessed indication of impedance, and
   determine a condition of the evacuated space of the vacuum interrupter based on the determined measure of impedance.

2. The sensing system of claim 1, wherein to determine a condition of the evacuated space, the processor determines whether a pressure of the evacuated space has increased based on the determined measure of impedance.

3. The sensing system of claim 1, wherein:
the indication of impedance comprises one of a voltage across the sensor or a current through the material, and
the determined measure of impedance comprises an impedance of the material.

4. The sensing system of claim 1, wherein the sensor comprises a plurality of contacts that are held in physical contact with each other, each of the plurality of contacts comprising the material that oxidizes in the presence of air.

5. The sensing system of claim 1, wherein the sensor comprises a contact and an endcap of the vacuum interrupter.

6. The sensing system of claim 1, wherein the electronic storage further stores a second measure of impedance, a threshold difference, and instructions that, when executed, cause the electronic processor to:
   compare the determined measure of impedance to the second measure of impedance to determine a difference in impedance,
   if the determined difference is equal to or greater than the threshold difference, generate a signal and provide the signal to a switchgear that includes the vacuum interrupter to take the switchgear out of service.

7. The sensing system of claim 6, wherein the second measure of impedance is a measure of impedance determined based on an accessed measure of impedance obtained from the sensor at an earlier time.

8. The sensing system of claim 1, wherein the electronic storage further stores a threshold measure of impedance and instructions that, when executed, cause the electronic processor to:
   compare the determined measure of impedance to the threshold measure of impedance,
   if the determined measure of impedance is equal to or greater than the threshold impedance, generate a signal that is sufficient to provide information to take a switchgear that includes the vacuum interrupter out of service.

9. A method of detecting a loss of vacuum in a vacuum interrupter, the method comprising:
   measuring an indication of impedance of a material that oxidizes in the presence of air and is enclosed in an evacuated space that is internal to a vacuum interrupter, wherein the material is initially non-oxidized and becomes oxidized in response to air entering the evacuated space;
   determining, based on the measured indication of impedance of the material, an indication of pressure of the evacuated space; and
   generating a signal that represents a condition of the evacuated space based on the determined indication of pressure.

10. The method of claim 9, wherein the measured indication of impedance comprises a temperature of the material.

11. The method of claim 9, wherein the measured indication of impedance is one or more of a voltage, a current, a conductivity, and a resistivity.

12. The method of claim 9, further comprising:
   measuring a second indication of impedance of the material that oxidizes in air;
   comparing the measured indication of impedance to the second measured indication of impedance to determine a difference between the second measured indication of impedance and the measured indication of impedance;
   comparing the magnitude of the difference to a threshold value; and
   when the magnitude of the difference equals or exceeds the threshold, generating a signal and provide the signal to a switchgear that includes the vacuum interrupter to take the switchgear out of service.

13. The method of claim 9, wherein:
the vacuum interrupter comprises main contacts that open to prevent current from flowing through the vacuum interrupter and close to permit current to flow through the vacuum interrupter, and
the material that oxidizes in air is separate and distinct from the main contacts.

14. The method of claim 9, wherein:
the vacuum interrupter comprises main contacts that open to prevent current from flowing through the vacuum interrupter and close to permit current to flow through the vacuum interrupter,
the indication of impedance comprises temperature, and
the material that oxidizes in air comprises a portion of the main contacts.

15. A vacuum interrupter comprising:
a stationary contact;
a movable contact configured to move relative to the stationary contact between an open position and a closed position, the stationary contact and the movable contact being separated in the open position and being in contact in the closed position;
a central shield configured to contain arcs that form between the stationary contact and the moveable contact when separated in the open position;
a second shield positioned such that the central shield is between the second shield and either the movable contact or the stationary contact;
a vessel that encloses the central shield, the movable contact, and the stationary contact in an evacuated space; and
a sensor configured to produce an indication of impedance of a region in the evacuated space, the sensor being separate and distinct from the second shield and the central shield, and the second shield being between the sensor and the central shield, wherein
   the sensor comprises a material that oxidizes in the presence of air and is configured to produce an indication of impedance of the material, the material being initially non-oxidized and becoming oxidized in response to air entering the evacuated space, or the sensor comprises a thermal sensor in an insulator that at least partially surrounds the vessel.

16. The vacuum interrupter of claim 15, wherein the sensor is configured to produce the indication of impedance in one or more of the open position and the closed position.

17. The vacuum interrupter of claim 15, wherein the indication of impedance is one or more of an amount of current passing through the sensor, a voltage across the sensor, a conductivity of the sensor, an impedance of the sensor, a temperature of the sensor, and a temperature of a region in the vicinity of the sensor or vacuum interrupter.

18. The vacuum interrupter of claim 15, wherein
the sensor comprises the material that oxidizes in the presence of air,
the sensor comprises contacts that are physically separated from each other by a gap, the contacts of the sensor being separate and distinct from the moveable contact and the stationary contact, and
the indication of impedance of a region in the evacuated space comprises a voltage across the gap between the contacts of the sensor.

19. The vacuum interrupter of claim 18, wherein the vessel comprises one or more endcaps, and one of the contacts of the sensor is one of the endcaps.

20. The vacuum interrupter of claim 15, wherein the sensor comprises the material that oxidizes in the presence of air and the indication of impedance comprises a breakdown voltage of the evacuated space.

21. The vacuum interrupter of claim 15, wherein the second shield is conductive.

22. A system comprising:
a vacuum interrupter comprising:
a stationary contact;
a movable contact configured to move relative to the stationary contact between an open position and a closed position, the stationary contact and the movable contact being separated in the open position and being in contact in the closed position; and
a vessel that encloses the movable contact and the stationary contact in an evacuated space;
an insulator that at least partially surrounds the vessel;
a thermal sensor configured to produce an indication of a temperature of a region that is in the evacuated space, the thermal sensor being positioned in the insulator and outside of the evacuated space; and
a control system coupled to the sensor and configured to receive data from and to provide data to the sensor, the control system comprising an electronic processor and an electronic storage that stores instructions that, when executed, cause the electronic processor to:
access the indication of the temperature of the region that is in the evacuated space, and
determine a condition of the evacuated space based on the accessed indication of temperature.

23. The system of claim 22, wherein the insulator comprises a solid insulation that encapsulates the vacuum interrupter, and the thermal sensor is embedded in the solid insulation.

24. The system of claim 22, wherein to determine a condition of the evacuated space, the control system is configured to compare the indication of the temperature of the region that is in the evacuated space to an indication of an ambient temperature measured by another thermal sensor.

25. The system of claim 22, wherein the indication of the temperature of the region that is in the evacuated space is tracked over time, and the condition of the evacuated space is determined based on whether or not the temperature of the region increases over time.

* * * * *